US011197843B2

(12) United States Patent
Ayalon

(10) Patent No.: US 11,197,843 B2
(45) Date of Patent: Dec. 14, 2021

(54) PROCESS FOR PRODUCING FUCOXANTHIN AND/OR POLYSACCHARIDES FROM MICROALGAE

(71) Applicant: ALGAHEALTH (AH) LTD., Misgav (IL)

(72) Inventor: Oran Ayalon, Mazkeret Batya (IL)

(73) Assignee: ALGAHEALTH (AH) LTD., Misgav (IL)

( * ) Notice: Subject to any disclaimer, the term of this patent is extended or adjusted under 35 U.S.C. 154(b) by 627 days.

(21) Appl. No.: 15/755,614

(22) PCT Filed: Aug. 23, 2016

(86) PCT No.: PCT/IL2016/050917
§ 371 (c)(1),
(2) Date: Feb. 27, 2018

(87) PCT Pub. No.: WO2017/037692
PCT Pub. Date: Mar. 9, 2017

(65) Prior Publication Data
US 2020/0230098 A1 Jul. 23, 2020

Related U.S. Application Data

(60) Provisional application No. 62/211,094, filed on Aug. 28, 2015.

(51) Int. Cl.
*A61K 31/336* (2006.01)
*C12P 7/62* (2006.01)
*C12N 1/12* (2006.01)
*C12N 1/02* (2006.01)
*B01D 11/04* (2006.01)
*B01D 15/08* (2006.01)
*A61K 9/00* (2006.01)

(52) U.S. Cl.
CPC .......... *A61K 31/336* (2013.01); *A61K 9/0014* (2013.01); *B01D 11/0403* (2013.01); *B01D 11/0492* (2013.01); *B01D 15/08* (2013.01); *C12N 1/02* (2013.01); *C12N 1/12* (2013.01); *C12P 7/62* (2013.01)

(58) Field of Classification Search
CPC ................ A61K 31/336; A61K 9/0014; A61K 2236/00; A61K 31/715; A61K 36/02; B01D 11/0403; B01D 11/0492; B01D 15/08; C12N 1/02; C12N 1/12; C12P 7/62; C12P 19/04; A61P 3/10; A61P 9/10; A61P 3/06; A61P 35/00; A61P 3/04; A61P 3/00; A61P 25/28; A61P 25/24; A61P 25/00; C07D 303/16

See application file for complete search history.

(56) References Cited

U.S. PATENT DOCUMENTS

| 4,871,551 | A | 10/1989 | Spencer |
| 5,378,369 | A | 1/1995 | Rose et al. |
| 5,529,911 | A | 6/1996 | Hohl |
| 5,591,343 | A | 1/1997 | Kitaoka et al. |
| 8,927,522 | B2 | 1/2015 | Coragliotti et al. |
| 2007/0167398 | A1 | 7/2007 | Dillon |
| 2010/0233761 | A1 | 9/2010 | Czartoski et al. |
| 2011/0086386 | A1 | 4/2011 | Czartoski et al. |
| 2011/0179699 | A1 | 7/2011 | D'Addario et al. |
| 2013/0309719 | A1 | 11/2013 | Griffiths |
| 2014/0051131 | A1 | 2/2014 | Dodd et al. |
| 2015/0065568 | A1 | 3/2015 | Uekita et al. |
| 2015/0119355 | A1 | 4/2015 | Bavington et al. |
| 2015/0140619 | A1 | 5/2015 | Reddy et al. |
| 2015/0225322 | A1 | 8/2015 | Looten et al. |

FOREIGN PATENT DOCUMENTS

| CA | 2 057 760 C | 3/2004 |
| CN | 103396979 B | 11/2014 |
| CN | 104531604 A | 4/2015 |
| EP | 0 612 725 A1 | 8/1994 |
| JP | S52-028989 A | 3/1977 |
| JP | H02-503632 A | 11/1990 |
| JP | H05-030987 A | 2/1993 |
| JP | H07-002761 A | 1/1995 |
| JP | H08-089280 A | 4/1996 |
| JP | 2008-184390 A | 8/2008 |
| JP | 2008-291004 A | 12/2008 |
| JP | 2010-209023 A | 9/2010 |
| JP | 2010-233517 A | 10/2010 |
| JP | 2012-520076 A | 9/2012 |
| JP | 2014-509188 A | 4/2014 |
| JP | 2014-520165 A | 8/2014 |
| JP | 2015-517587 A | 6/2015 |
| KR | 10-1410632 B1 | 6/2014 |
| KR | 10-1413874 B1 | 7/2014 |
| WO | 2007136428 A2 | 11/2007 |

(Continued)

OTHER PUBLICATIONS

KR101413874 B1; machine translation (Year: 2014).*

(Continued)

*Primary Examiner* — Jason Deck
(74) *Attorney, Agent, or Firm* — J.A. Lindeman & Co. PLLC

(57) ABSTRACT

Provided is a process for production of fucoxanthin and/or polysaccharides from microalgae and the use of purified fucoxanthin thereof in pharmaceutical, cosmetic, nutraceutical and food compositions.

17 Claims, 14 Drawing Sheets

(56) References Cited

FOREIGN PATENT DOCUMENTS

| WO | 2012101459 A2 | 8/2012 |
| WO | 2013161378 A1 | 2/2013 |
| WO | 2014/003740 A1 | 1/2014 |
| WO | 2014/078459 A1 | 5/2014 |

OTHER PUBLICATIONS

Yang et al., (2010) Aggregate formation and polysaccharide content of Chlorella pyrenoidosa Chick (Chlorophyta) in response to simulated nutrient stress. Bioresource Technology 101(21): 8336-8341.

Zang (2014); Screening and pilot culture of fucoflavin-rich microalgae Full text database of Chinese excellent master's thesis No. 10, pp. A006-A316. 21 pages. With English translation.

Martin, (2015) Fucoxanthin and its metabolite fucoxanthinol in cancer prevention and treatment. Marine drugs, 13(8), 4784-4798.

* cited by examiner

FIG.3 Cont.

| Peak Name | Area | Retention time (RT), min | Concentration, % |
|---|---|---|---|
| n.d | 0.102 | 6.12 | 0.38 |
| Fucoxanthin | 26.457 | 9.57 | 97.42 |
| n.d | 0.07 | 10.35 | 0.26 |
| n.d | 0.032 | 11.05 | 0.12 |
| n.d | 0.497 | 11.58 | 1.82 |
| Total | 27.158 | | 100 | n.d = not determined

Fig 6 Cont.

| Area | Peak Name | Retention time (RT), min | Concentration % |
|---|---|---|---|
| 0.37 | n.d | 6.97 | 3.67 |
| 6.03 | Fucoxanthin | 9.57 | 59.81 |
| 0.182 | n.d | 11.06 | 1.80 |
| 0.874 | n.d | 11.59 | 8.67 |
| 1.038 | n.d | 12.19 | 10.30 |
| 0.055 | n.d | 12.88 | 0.54 |
| 0.246 | n.d | 13.99 | 2.44 |
| 0.118 | n.d | 20.73 | 1.17 |
| 0.602 | Chlorophyll A | 21.69 | 5.97 |
| 0.046 | n.d | 22.23 | 0.46 |
| 0.064 | n.d | 22.43 | 0.63 |
| 0.044 | n.d | 24.17 | 0.46 |
| 0.062 | n.d | 24.65 | 0.61 |
| 0.351 | n.d | 26.31 | 3.48 |
| Total: 10.082 | | | Total: 100 | n.d = not determined

PROCESS FOR PRODUCING FUCOXANTHIN AND/OR POLYSACCHARIDES FROM MICROALGAE

TECHNICAL FIELD

The present invention relates to the field of biotechnology and more particularly to an improved process for production of fucoxanthin and/or polysaccharides from microalgae.

BACKGROUND OF THE INVENTION

Microalgae are autotrophic photosynthetic microorganisms that have the ability to grow autonomously by photosynthesis. Microalgae develop in marine aquatic media and in fresh or brackish waters, as well as in various land habitats. Most species of the microalgae found in fresh water or in the oceans are generally autotrophic, i.e. they can only grow by photosynthesis. For these species, the presence of organic carbon-containing substrates or organic matter in their environment is not favorable, and does not improve growth. However, a certain number of species of microalgae are not found to be strictly autotrophic. Thus, some of these species that are heterotrophic are capable of developing by fermentation (i.e., by using organic matter) in the total absence of light.

Other species of microalgae, for which photosynthesis remains essential for development, are capable of benefiting both from photosynthesis and from organic matter present in the microalgae environment. These intermediate species, are said to be mixotrophic, and can be cultured in the presence of both light and organic matter.

Fucoxanthin is a xanthophyll, which is found as a pigment in the chloroplasts of brown algae having brown or green color. It belongs to the family of carotenoids and has a molecule structurally similar to that of beta-carotenes. Fucoxanthin does not possess vitamin-like activity in the human body and it believed to act as an antioxidant. The human consumption of fucoxanthin is associated with several health benefits.

Fucoxanthin absorbs light primarily in the blue-green to yellow-green part of the visible spectrum, peaking at around 510-525 nm and absorbing in the range of 450 to 540 nm. Fucoxanthin is abandon in brown seaweeds (macroalgae from the family Phaeophyceae) and in diatoms (microalgae from the family Bacillariophyta). It is also present in golden-brown microalgae such as *Isochrysis* sp.

The structural formula of fucoxanthin is the following:

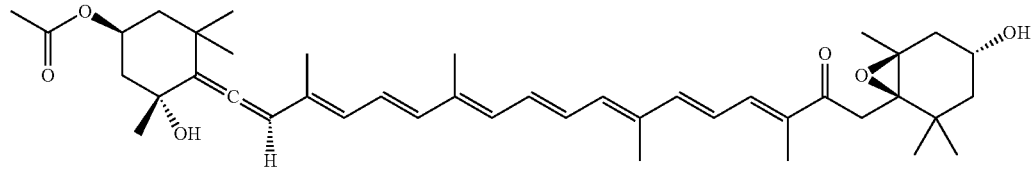

The chemical formula of fucoxanthin is $C_{42}H_{58}O_6$ and its chemical name is [(1S,3R)-3-hydroxy-4-[(3E,5E,7E,9E,11E,13E,15E)-18-[(1R,3S,6S)-3-hydroxy-1,5,5-trimethyl-7-oxabicyclo[4.1.0]heptan-6-yl]-3,7,12,16-tetramethyl-17-oxooctadeca-1,3,5,7,9,11,13,15-octaenylidene]-3,5,5-trimethylcyclohexyl] acetate.

Fucoxanthin has an allenic moiety in its molecule in addition to 7 conjugated double bonds, epoxy, hydroxyl, ketonic carbonyl and carboxyl ester moieties that contribute to its unique structure.

Carotenoids in general and fucoxanthin in particular are widely used commercially as active pharmaceutical ingredients, dietary supplements, nutraceuticals, food additives (e.g., in Japanese cuisine), in cosmetics and as additives in animal feed.

As recited in Publications WO2014/003740 and WO2014/078459, carotenoids such as fucoxanthin may be effective in promoting weight loss. A typical formulation includes a fat blocker, a filler component, an insulin sensitizer, and a fat growth suppressant, wherein the fat blocker may include a carotenoid such as fucoxanthin or punicic acid. This use may be due to the ability of the human body to store metabolites of fucoxanthin in fat cells for prolonged period of time, which may induce fat loss while inhibiting fat cell differentiation and proliferation.

In addition, fucoxanthin possesses other health benefits, such as correcting abnormalities in glucose metabolism in muscle tissue, which can help diabetics and reduce blood levels of cholesterol and triglycerides of humans by mechanisms that are currently unverified.

Reductions in blood pressure, liver fat stores and liver enzyme values have been noted with fucoxanthin supplementation in humans.

Several research groups have studied the anti-inflammatory, anti-nociceptive, and anti-cancer effects of fucoxanthin. One study has shown that fucoxanthin may have an effect on oxidative stress-related diseases in addition to its anti-cancer effect in some cases by inducing apoptosis of various cancer cells or by exerting an inhibitory effect on the invasiveness of cancer cells by suppressing the expression of the gelatinolytic enzyme MMP-9 and by suppressing the mobility of melanoma cells.

For example, L. J Martin in "Mar Drugs, 2015 Jul. 31; 13(8); 4784-98 describes in an article entitled "Fucoxanthin and its metabolite fucoxanthinol in cancer prevention and treatment" that fucoxanthin is metabolized mainly to fucoxanthinol by digestive enzymes of the gastrointestinal tract. These compounds have been shown to possess many beneficial health effects, including anti-mutagenic, anti-diabetic, anti-obesity, anti-inflammatory and anti-neoplastic actions. In this review, the author addresses the mechanisms of action of fucoxanthin and fucoxanthinol according to different types of cancers. Current findings suggest that these compounds are effective for the treatment and/or prevention of cancer development and aggressiveness.

The use of seaweeds for producing fucoxanthin has several disadvantages. The content of fucoxanthin in various parts of the seaweed is low, that is, about 0.01-0.3% of the dry weight. Therefore, the extraction of fucoxanthin from seaweed is cumbersome on commercial scale so that about two tons of dry seaweeds are used in order to produce 1 Kg of 5% fucoxanthin oleoresin (0.0025% yield). In addition, seaweeds harvest is limited to the fall and winter seasons and cannot be carried out in other seasons and therefore the producing plant may operate not on full capacity all year round. Another problem is concerned with the inability of controlling the growth conditions of the seaweeds in the oceans that are becoming increasingly contaminated. Moreover, seaweeds growing in the oceans tend to sequester contaminants such as heavy metals (e.g., mercury and cadmium), iodine, polycyclic aromatic hydrocarbons (PAHs) and radioactive contaminations.

Therefore, microalgae are preferable for production of fucoxanthin. However, the present methods known in the art for producing fucoxanthin from microalgae afford the product in relatively low yields and purity. For example, C. M. Reddy et al. describe in US Publication 2015/0140619, production of biofuel from the microalgae *Isochrysis* sp. The fucoxanthin is a co-product of the process, which is not efficient because the concentration of the isolated fucoxanthin is very low, i.e., 0.3-2 mg/g.

Thus, there is a need in the art for an efficient process for production of fucoxanthin that will afford highly pure fucuxanthin in relatively high yield. The present invention provides such a process.

BRIEF SUMMARY OF THE INVENTION

The present invention provides an improved process for producing fucoxanthin and/or polysaccharides in high yield and purity.

According to some embodiments of the present invention, dry microalgae powder rich in fucoxanthin and/or polysaccharides and/or oleoresin rich in fucoxanthin and other compounds such as polyunsaturated fatty acids (PUFA) and/or solutions rich in polysaccharides and/or sulfated polysaccharides are provided by the process disclosed herein.

Applicant has developed an improved process for producing fucoxanthin and/or polysaccharides from microalgae comprising the following steps:
  (a) Cultivating the microalgae medium using inducers to enable rapid cell growth for enhanced production of fucoxanthin and/or polysaccharides;
  (b) Harvesting and drying the algal culture to produce a dry culture;
  (c) Carrying out air pressure milling to crack the cell walls of the algae;
  (d) Extracting the dry culture to produce extracts rich in fucoxanthin and/or in polysaccharides; and
  (e) Separating the extraction mixture into a biomass fraction and a fucoxanthin-rich oleoresin and/or polysaccharide-rich extract and optionally further purifying said fucoxanthin-rich oleoresin and/or polysaccharide-rich extract.

According to preferred embodiment of the present invention, the process provided herein affords crude product containing at least about 1.5% fucoxanthin in the dry biomass and at least about 10% fucoxanthin in the extract.

According to some embodiments of the present invention, fucoxanthin is separated from the polysaccharides and purified by a method selected from filtration, gel-filtration on columns using, e.g., natural silica beads as medium for filtration, ion-exchange chromatography, liquid chromatography methods including preparative TLC or preparative HPLC and combination of methods thereof to afford highly pure fucoxanthin.

According to some embodiments of the present invention, highly pure fucoxanthin, obtained by, e.g., liquid chromatography, is used alone or in combination with other active ingredients in formulations for preventing, ameliorating or treating a condition or disease selected from cancer, metabolic syndrome including overweight, obesity, high blood cholesterol LDL, high-blood triglycerides, diabetes type II, insulin resistant diabetes, high-blood sucrose, atherosclerosis, dementia, Alzheimer's disease, loss of memory, multiple-sclerosis, depression including environmental-stress, heat stress and general neuroprotection.

The present invention provides pharmaceutical compositions that contain highly pure fucoxanthin produced as described herein in admixture with pharmaceutically acceptable excipients and, optionally, other therapeutic agents.

According to some embodiments, the pharmaceutical compositions of the present invention that can be formulated dosage forms are administered, for example, as tablets, pills, powders, granules, dragees, liquids, suspensions, emulsions, granules, capsules, suppositories, injection preparations (solutions and suspensions), patches and the like.

According to some embodiments, the fucoxanthin of the present invention is used alone or in combination with other active ingredients in cosmetic preparations such as ointments, gels, creams, solutions, emulsions, lotions and the like for topical or other forms of administration to be used as anti-aging, skin-whitening, skin protection and other cosmetic uses.

In some embodiments, pharmaceutical compositions comprising the fucoxanthin of the present invention are prepared by mixing said fucoxanthin with at least one additional active ingredient selected from absorption accelerators, binders, bulking agents, carriers, coating agents, diluents, disintegrants, extenders, fillers, flavoring agents, lubricants, surface-active agents, wetting agents and the like.

According to some embodiments, nutraceuticals, dietary supplements or food preparations comprising the fucoxanthin of the present invention are prepared by mixing said fucoxanthin and/or polysaccharides with food ingredients such as sugars and starches, dietary fibers, lipids, amino acids, proteins such as protein isolates or protein hydrolyzates, lactic acid, vitamins, minerals and other ingredients that are commonly used in such preparations.

According to some embodiments, the dietary supplements of the present invention may include, for example, a beverage, a soup, a snack, a dairy product and the like.

DETAILED DESCRIPTION OF THE INVENTION

The present invention provides an improved process for producing fucoxanthin and/or polysaccharides in high yield and purity.

According to some embodiments of the present invention, dry microalgae powder rich in fucoxanthin and/or polysaccharides and/or solid oleoresin rich in fucoxanthin and other compounds such as polyunsaturated fatty acids (PUFA) and/or solutions rich in polysaccharides and/or sulfated polysaccharides are provided by the process disclosed herein.

Applicant has developed an improved process for producing fucoxanthin and/or polysaccharides from microalgae comprising the following steps:
(a) Cultivating the microalgae medium using inducers to enable rapid cell growth for enhanced production of fucoxanthin and/or polysaccharides;
(b) Harvesting and drying the algal culture to produce a dry culture;
(c) Carrying out air pressure milling to crack the cell walls of the algae;
(d) Extracting the dry culture to produce extracts rich in fucoxanthin and/or polysaccharides; and
(e) Separating the extraction mixture into a biomass fraction and a fucoxanthin-rich oleoresin and/or polysaccharide-rich extract and optionally further purifying said fucoxanthin-rich oleoresin and/or polysaccharide-rich extract.

Figure 1:
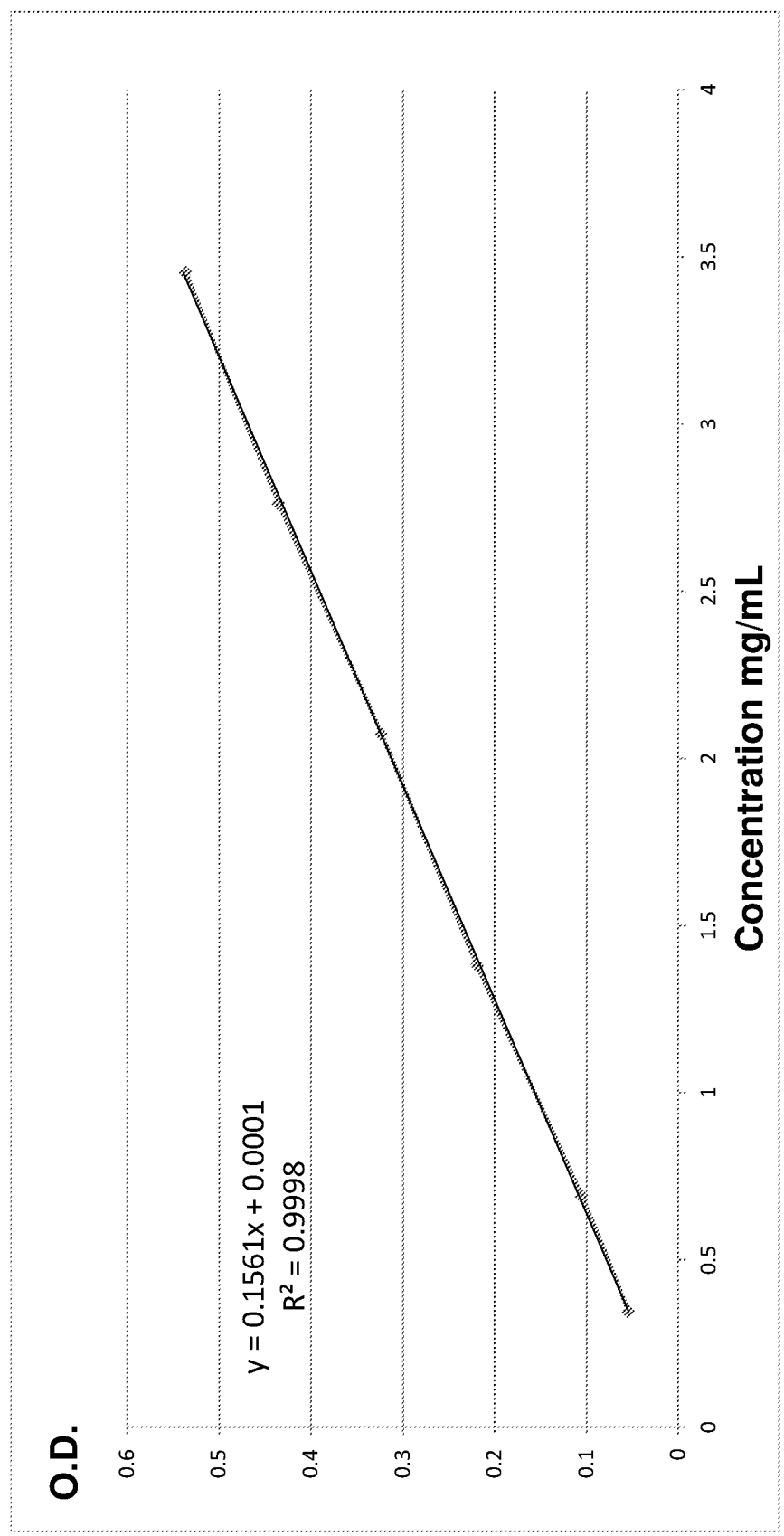
FIG. 1 depicts the fucoxanthin HPLC calibration curve using acetone/methanol/hexane as solvent.
Figure 2:
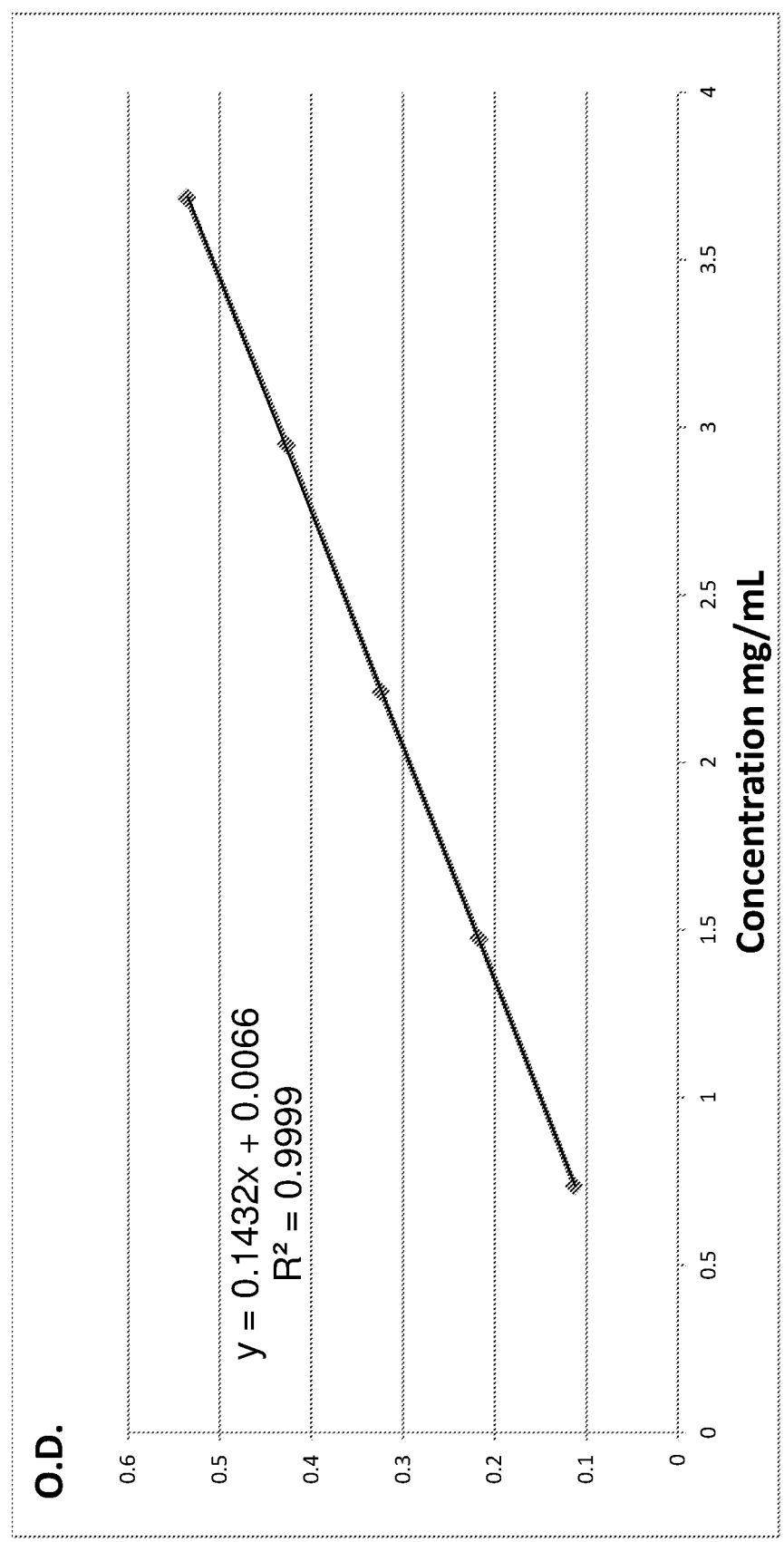
FIG. 2 depicts the fucoxanthin HPLC calibration curve using acetonitrile as solvent.
Figure 3:
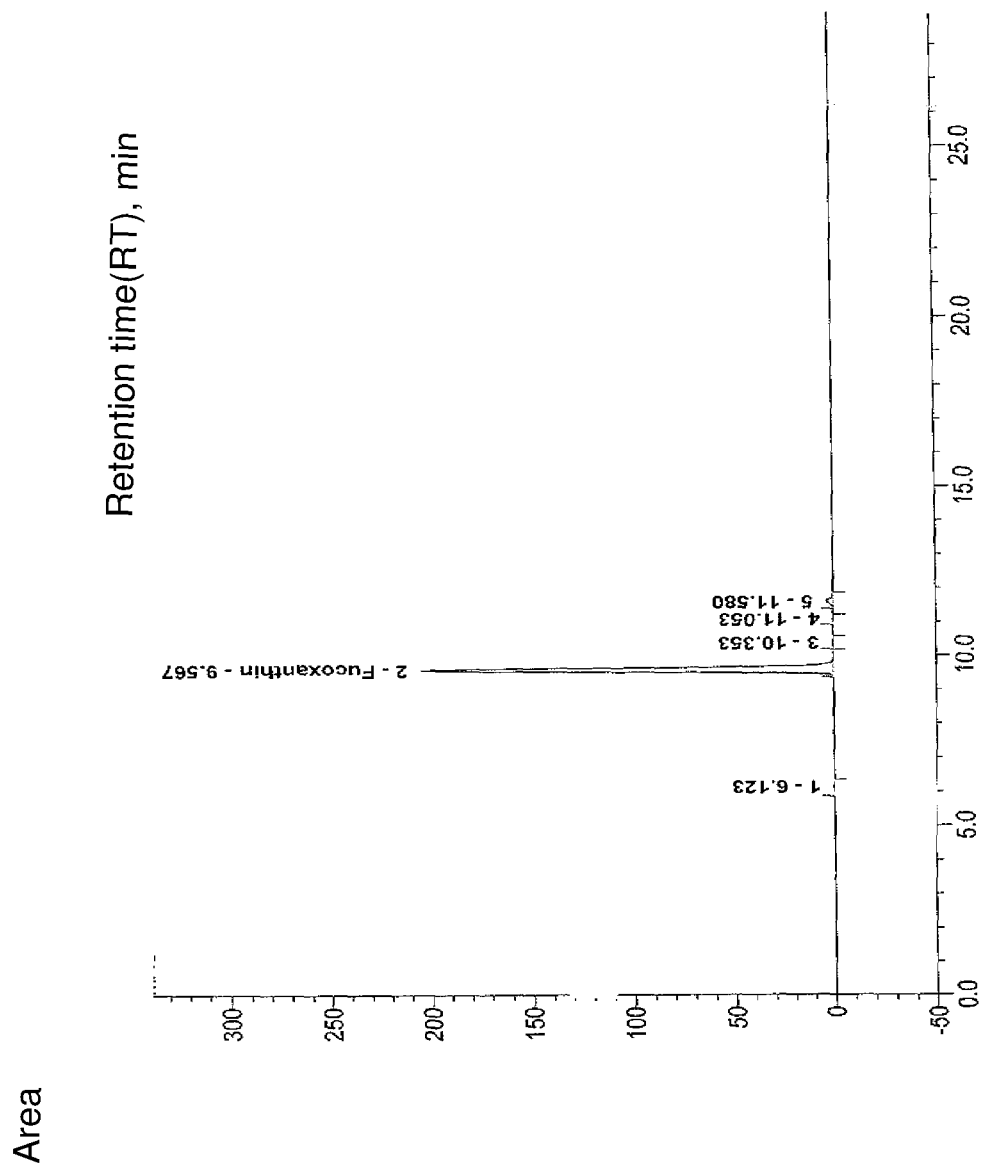
FIG. 3 depicts an HPLC chromatogram of fucoxanthin solution having concentration of 3.686 mg/mL.
Figure 4:
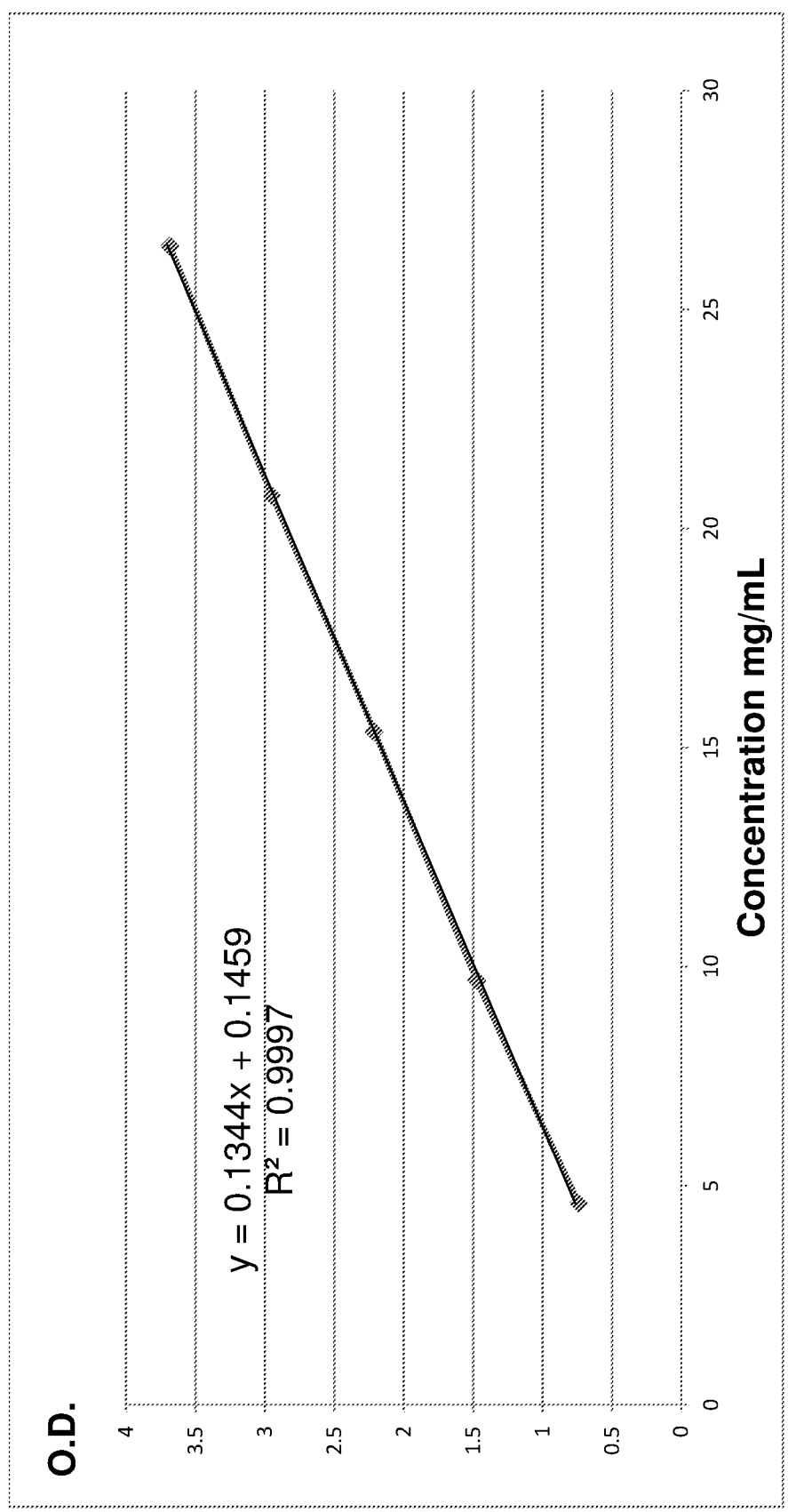
FIG. 4 depicts the chlorophyll A calibration curve.
Figure 5:
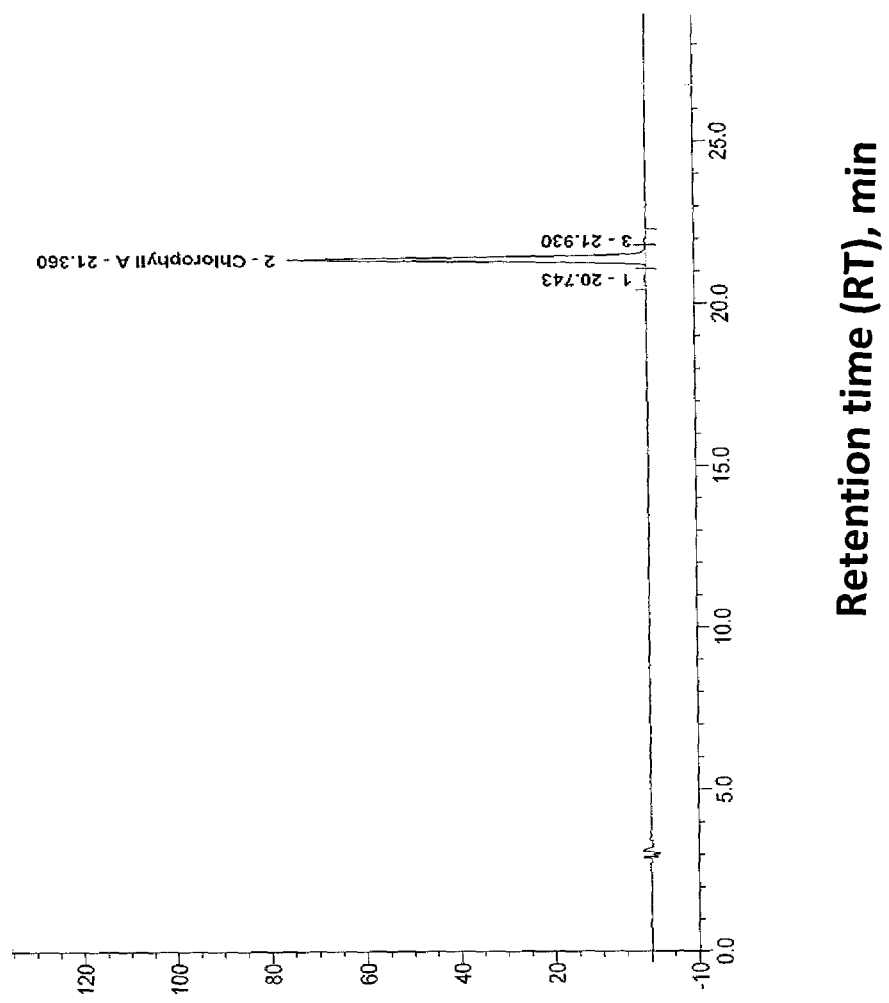
FIG. 5 depicts the HPLC chromatogram of chlorophyll A at 450 nm.
Figure 6:
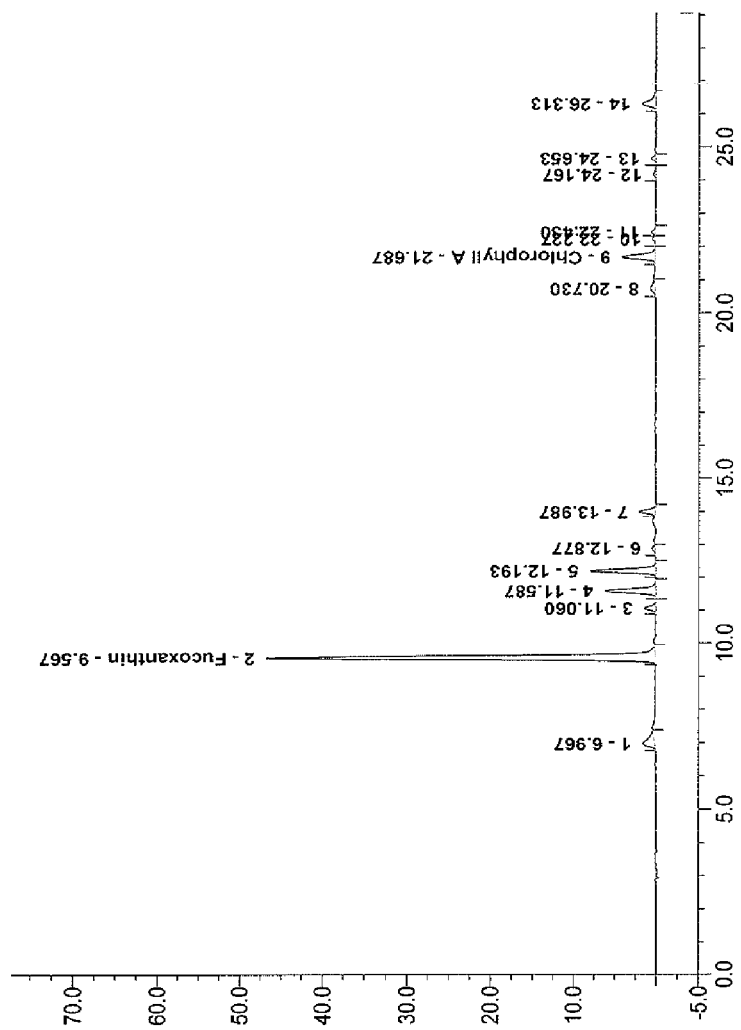
FIG. 6 depicts the chromatogram of freeze-dried extracted fucoxanthin oleoresin that includes chlorophyll A.
Figure 7:
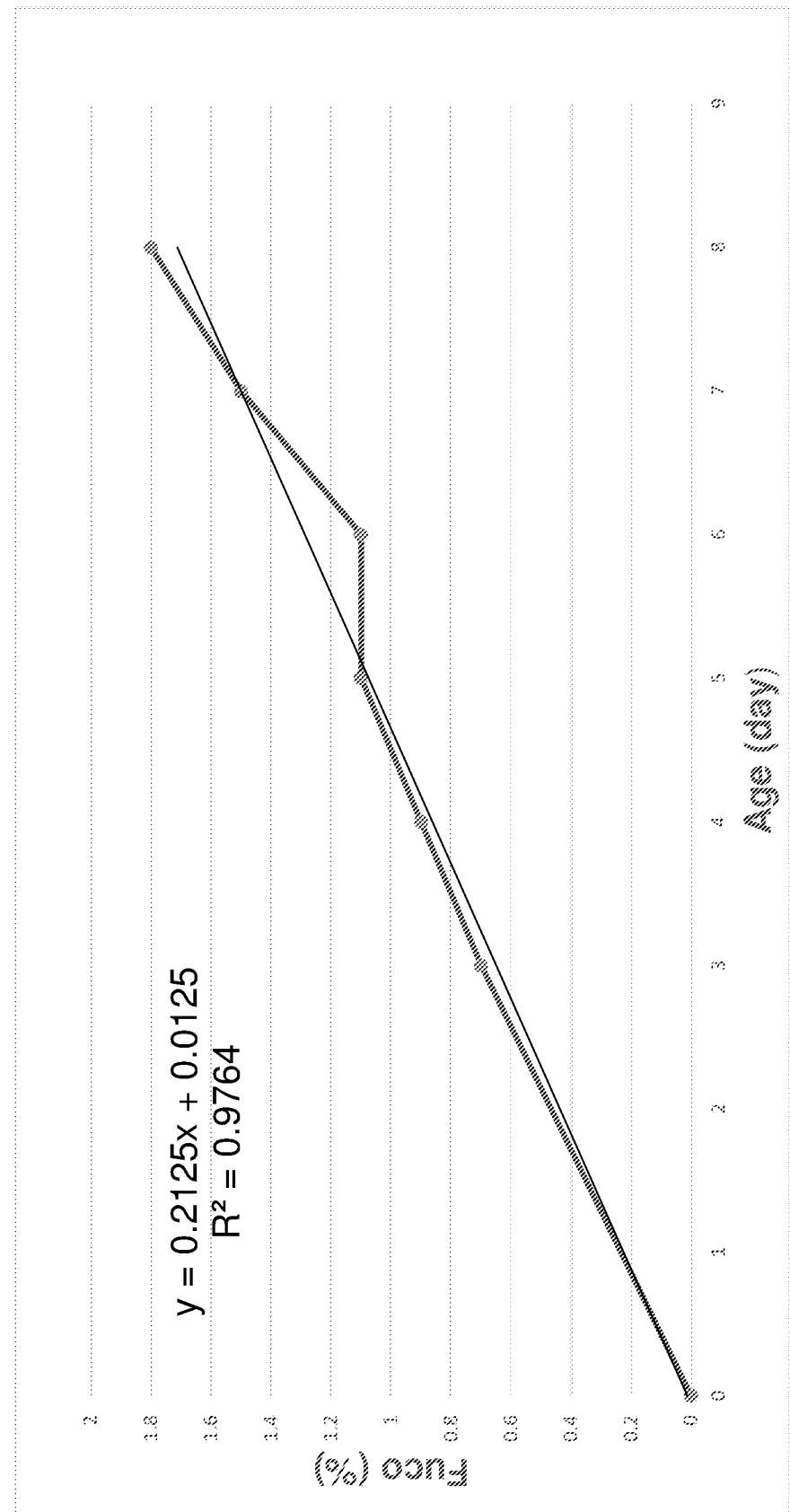
FIG. 7 depicts the *Isochrysis* sp. growth curve in outdoor flat panels of 100 L under nitrate starvation, expressed as % of accumulated fucoxanthin vs. age (day).

According to the present invention, as used herein, the term Optical Density (O.D) relates to the absorbance measured in a spectrophotometer at wavelength of, e.g., 450 nm of e.g., fucoxanthin samples (FIGS. 1 and 2) or, e.g., chlorophyll A sample (FIG. 4) using solutions of variable concentrations.

According to the present invention, as used herein, the term supernatant refers to the remaining solution or liquid obtained by centrifugation or precipitation.

According to the present invention, as used herein, calibration curve is a method of determining the concentration of a substance in an unknown sample by comparing the unknown to a set of samples of known concentrations.

According to the present invention, as used herein, supercritical fluid extraction (SFE) is a process of separating one component (the extractant) from another (the matrix) using supercritical fluids as the extracting solvent. Extraction is from a solid matrix, but can also be from liquids. SFE can be used to either strip unwanted material from a product (e.g., decaffeination) or to collect a desired product (e.g., an essential oil). Usually, liquid carbon dioxide ($CO_2$) is one of the most used supercritical fluids.

According to the present invention, as used herein, auxins are plant brassinosteroidal hormones that are added to induce higher rates of biomass acquisition.

According to the present invention, as used herein, the term growth medium refers to either growth medium or culture medium that are liquid or gel mixtures that support the growth of microorganisms or cells or small plants by using specific cell types derived from plants and microbiological culture, which are used for growing, e.g., microalgae and microorganisms.

According to an aspect of the present invention, the microalgae is selected from *Phaeodactykum* sp., *Isochrysis* sp., *Amphora* sp., *Naviculla lensi*, *Naviculla incerta* and *Chaeotocerous* sp.

According to another aspect of the present invention, cultivating the microalgae is carried out in a medium that induces growth, thus enabling rapid cell development and mass acquisition.

According to some embodiments of the present invention, cultivating the microalgae is carried out using stress conditions (that induce the synthesis and accumulation of fucoxanthin) selected form nitrogen or nitrate starvation, phosphorous starvation, light starvation, selecting specific light wavelengths, changing the light wave-length during cultivation (e.g., from blue-green to green-red), adding $H_2O_2$, applying heat, using higher pH values (up to 9.0), adding chlorine ions, adding plant hormones (such as auxins and cytokinins), exposing the medium to ozone and combination of stress conditions thereof.

According to some embodiments of the present invention, cultivating microalgae is carried out in open, closed, or semi-closed systems.

According to a specific embodiment of the present invention, cultivating the microalgae is carried out in an open system.

According to a specific embodiment of the present invention, cultivating the microalgae is carried out in a closed system.

According to a specific embodiment of the present invention, cultivating the microalgae is carried out in a semi-closed system.

Figure 8:
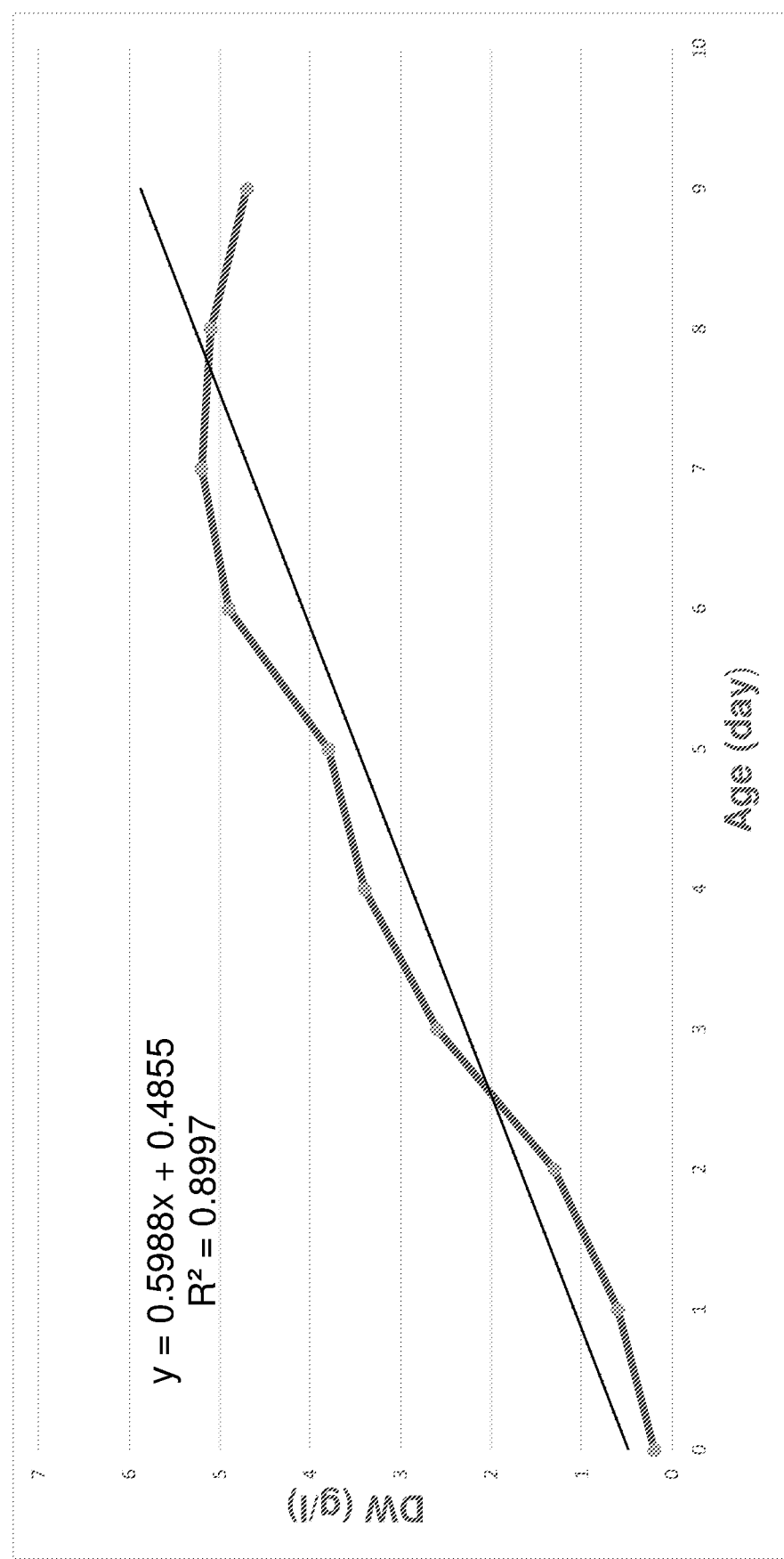
FIG. 8 depicts the *Isochrysis* sp. growth curve in outdoor flat panels of 100 L under nitrate starvation, expressed as dry weight (DW) vs. age (day).
Figure 9:
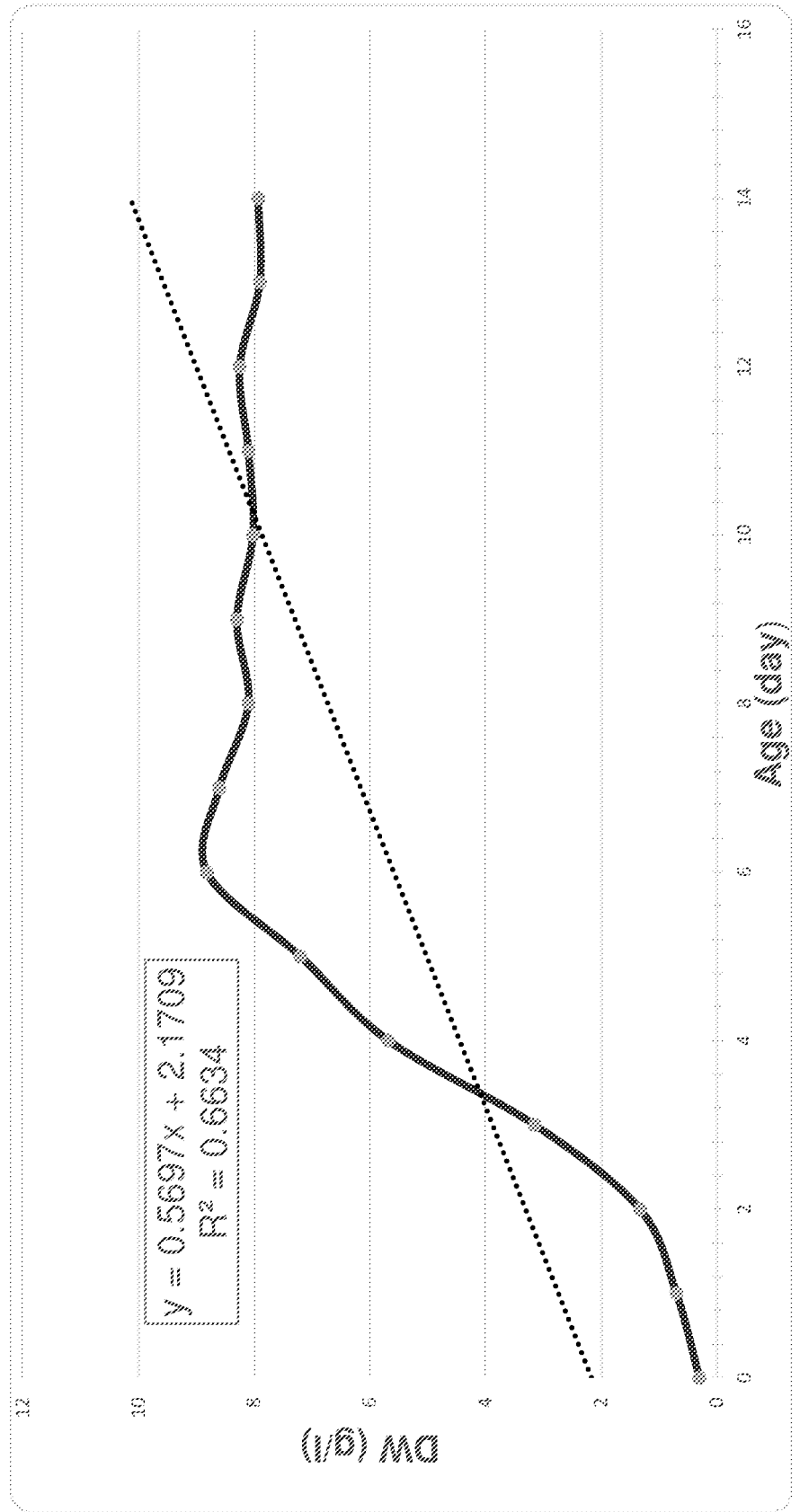
FIG. 9 depicts the *Isochrysis* sp. (induced with addition of auxin) growth curve expressed as dry weight (DW) vs. age (day).
Figure 10:
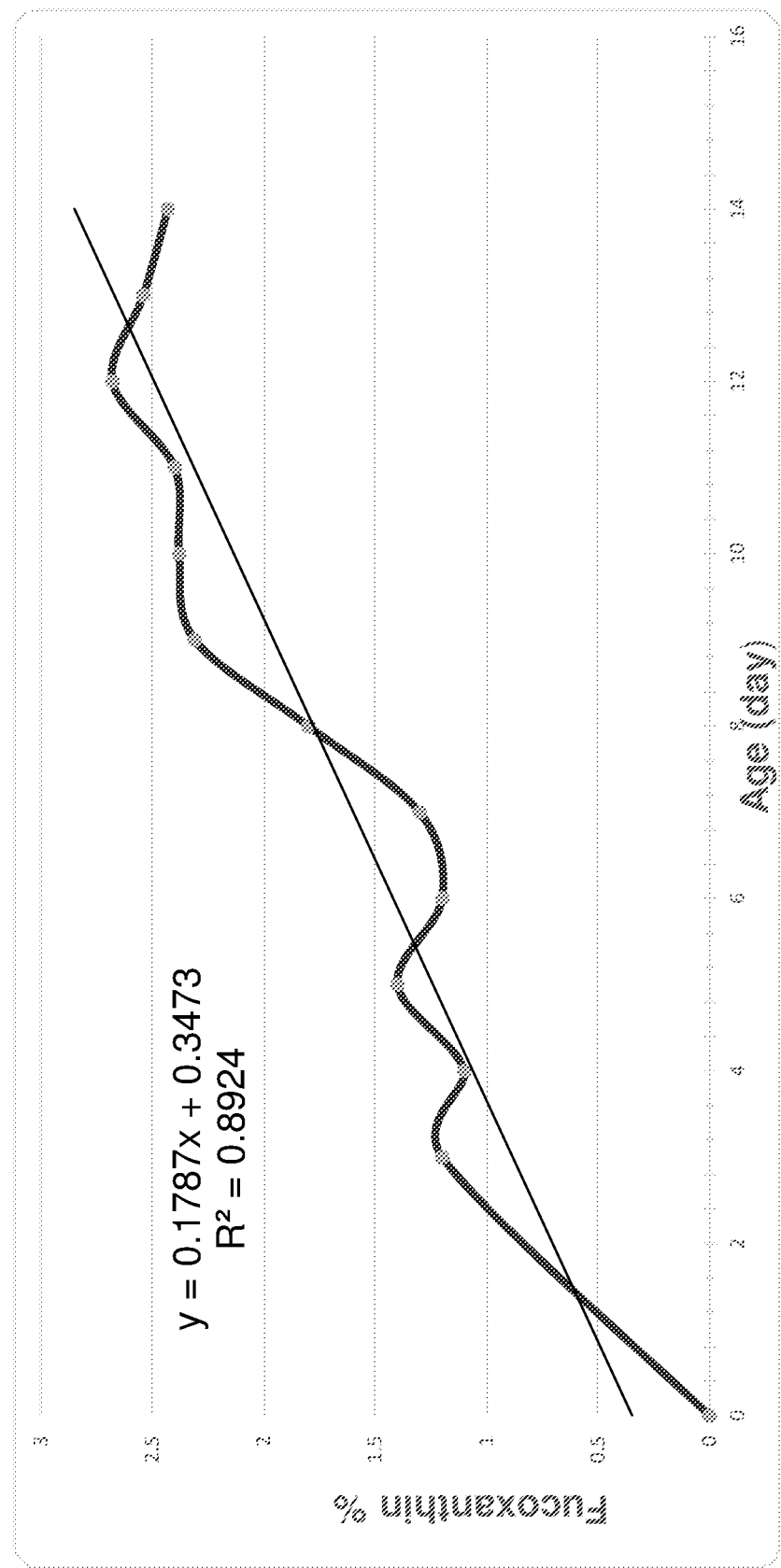
FIG. 10 depicts the *Isochrysis* sp. (induced with starvation of blue-green light and high pH) growth curve expressed as % of fucoxanthin vs. age (day).
Figure 11:
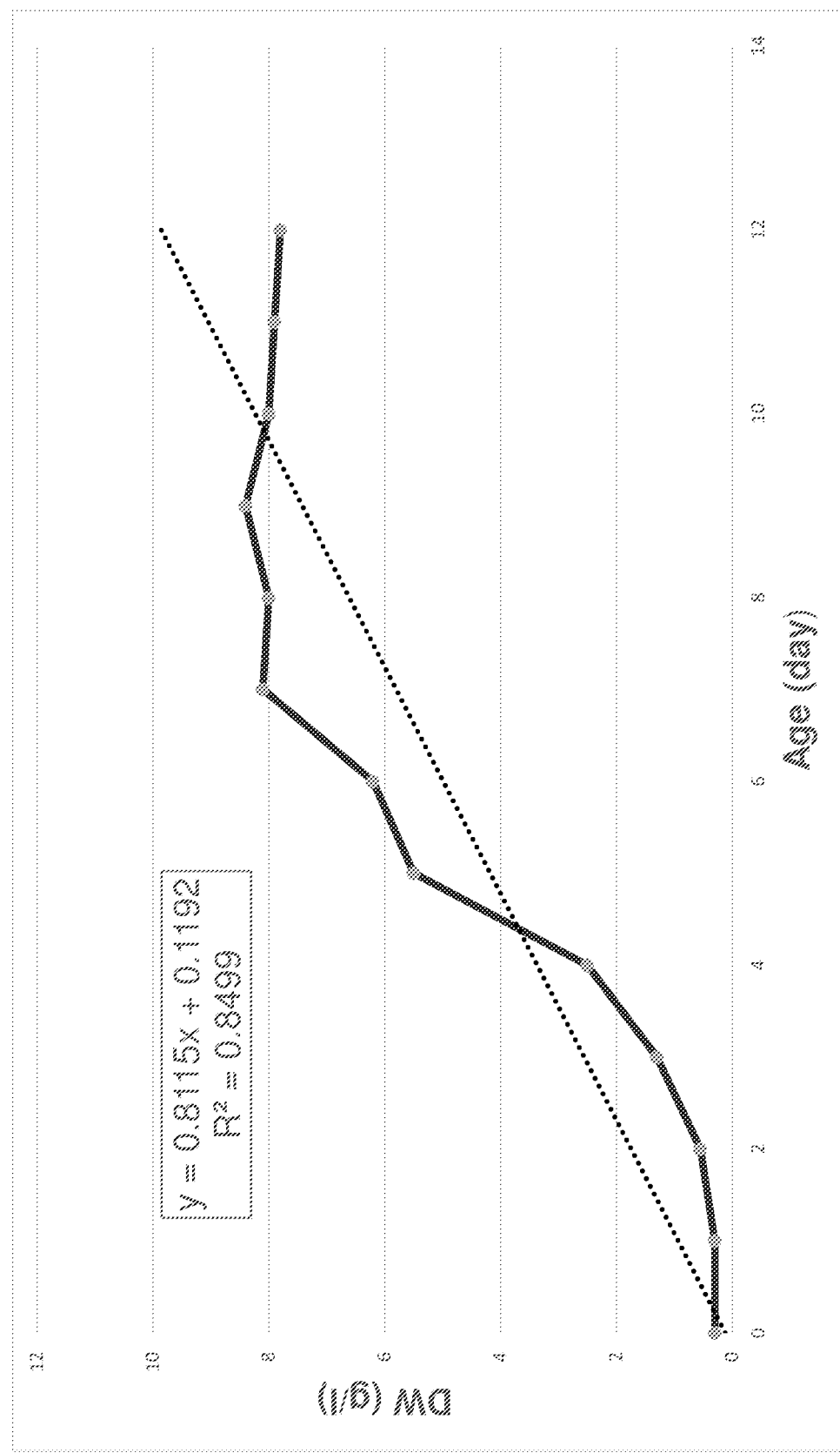
FIG. 11 depicts the *Amphora* sp. (induced with addition of auxin) growth curve expressed as dry weight (DW) vs. age (day).
Figure 12:
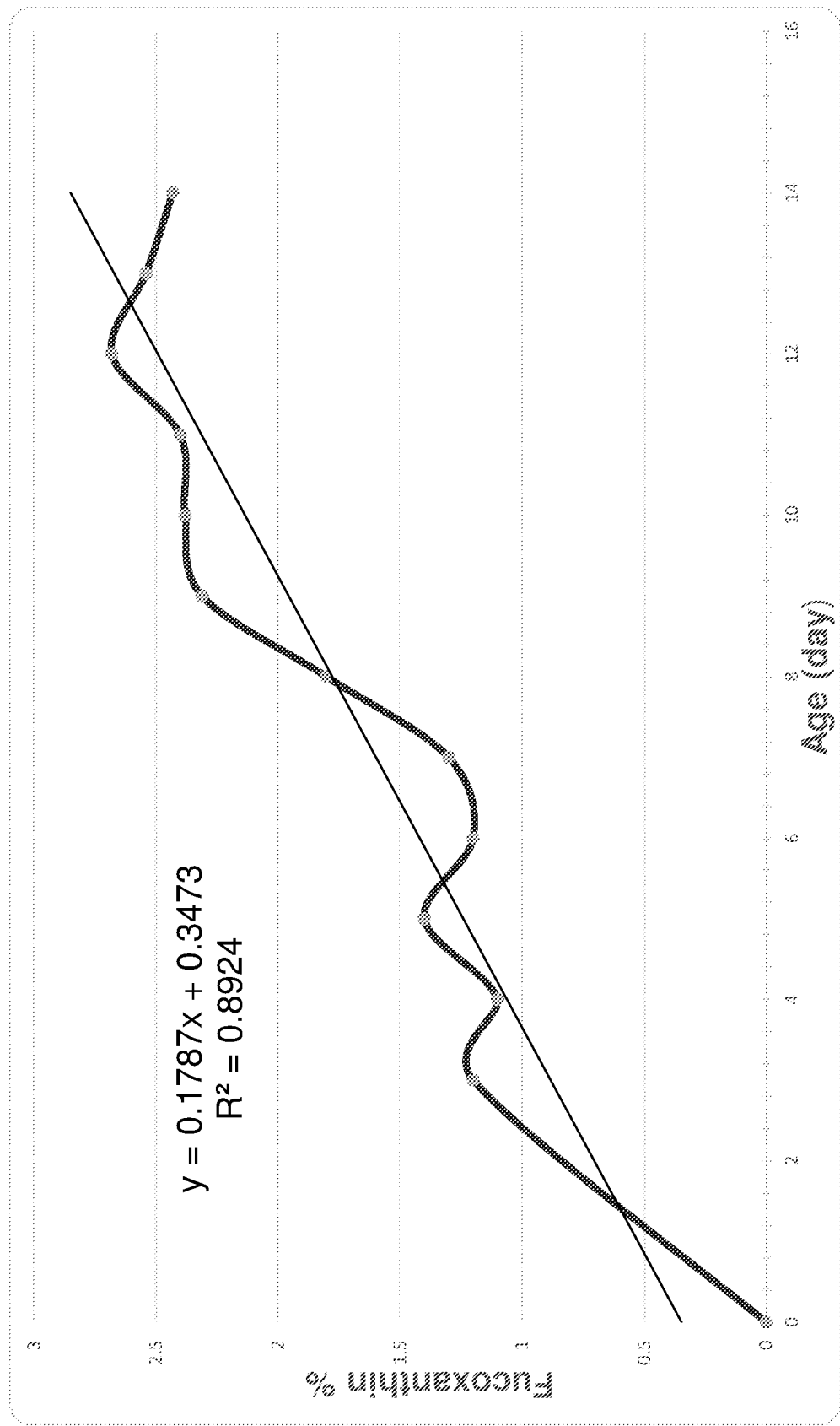
FIG. 12 depicts the *Amphora* sp. (induced with starvation of blue light and high pH) growth curve expressed as dry weight (DW) vs. age (day).

FIGS. 7-12 show that combinations of stress factors such as nitrate starvation, using higher temperatures (application of heat), using higher pH values (up to 9.0) and changes in the wavelengths (color) of the light (to blue-green or to green-red) cause inhibition of the growth of the algae along with induced accumulation of fucoxanthin. The accumulation of dry matter (DW) in, e.g., FIGS. 8, 11 and 12 is rapid until day 6, after which time it becomes constant.

Example 3 demonstrates the impact of inducing nitrate starvation on *Isochrysis* sp. as well the impact of inducing changes in light wavelengths on *Isochrysis* sp. grown with addition of auxins, as detailed in Table 1:

TABLE 1

| Parameter | Induction of nitrate starvation | Induction of changes in light wavelengths |
|---|---|---|
| Dry weight gain | 0.75 g/L/day | 1.4 g/L/day |
| Fucoxanthin gain | 8.38 mg/L/day | 16.41 mg/L/day |
| Fucoxanthin induction | 1.57 mg/L/day | 11.77 mg/L/day |
| Harvested fucoxanthin | 79.2 mg/L | 176.7 mg/L |

Example 3 further demonstrates the impact of inducing nitrate starvation on *Amphora* sp. as well as the impact of inducing changes in light wavelengths and using high pH on *Amphora* sp. grown with auxin, as detailed in Table 2 below.

TABLE 2

| Parameter | Induction of nitrate starvation | Induction of changes in light wavelengths |
|---|---|---|
| Average dry weight gain | 0.67 g/L/day | 1.16 g/L/day |
| Average fucoxanthin gain | 9.26 mg/L/day | 18.52 mg/L/day |
| Average fucoxanthin induction | 2.05 mg/L/day | 8.98 mg/L/day |
| Average harvested fucoxanthin | 73.8 mg/L | 169.3 mg/L |

According to specific embodiment of the present invention, the addition of plant brassinosterodial hormones, such as cytokinins and auxins, during the first cultivating stage results in higher rates of biomass acquisition.

According to a specific embodiment of the present invention, harvesting the microalgae is carried out by separating the microalgae from the aqueous mixture by centrifugation in, e.g., an industrial centrifuge followed by drying.

According to some embodiments of the present invention, drying is carried out by at least one method selected from lyophilization, spray drying, evaporation, air or vacuum drying, exposure to hot air, refractory window belt drying, drying in an oven and combination of methods thereof.

According to another aspect of the present invention, harvesting the microalgae is carried out by separating water from the microalgae by, e.g., centrifugation, scale of which depends on the microalgae species and the salinity of the cultivation medium.

According to another aspect of the present invention, the harvested biomass is concentrated into a solid, then washed with water in order to reduce salinity and optionally re-centrifuged to afford a product containing at least 10% solids, preferably at least 30% solids and most preferably of at least 45% solids.

According to another aspect of the present invention, the supernatant obtained by centrifugation and optionally re-centrifugation of the harvested biomass is used for purification of secreted polysaccharides.

According some embodiments of the present invention, fucoxanthin is separated from the proteins and extracted using organic solvents and/or supercritical fluids (SCF) such as liquid $CO_2$.

According to some embodiments of the present invention, the solvent used for extraction is selected from ethanol, isopropyl alcohol, n-butanol, diethyl ether, diisopropyl ether, n-pentane, n-hexanes, n-heptane, cyclohexane, petroleum ether, tetrahydrofuran, methyltetrahydrofuran, acetonitrile, acetone, methylethyl ketone, methylisobutyl ketone, ethyl acetate, n-propyl acetate, isopropyl acetate and mixtures of solvents thereof.

According to an aspect of the present invention, phosphoric acid is added to the solvent used for extraction.

According to some embodiments of the present invention, an edible oil selected from soya oil, corn oil, sunflower oil, sesame oil and combinations thereof is used as solvent for the extraction or used as co-solvent.

According to some embodiments of the present invention, the SCF solvent used for extraction of fucoxanthin-enriched oleoresin from the microalgae dry biomass is selected from liquid $SCF-CO_2$, butane, propane, $N_2O$ and the like, preferably liquid $SCF-CO_2$.

According to another aspect of the present invention, the supercritical fluid extraction (SFE) conditions for the supercritical $CO_2$ are above the critical temperature of 31° C. and critical pressure of 74 bars.

According to another aspect of the present invention, the solvent is passed through the dried algal matrix using an extraction pressure in the range of about 500-1000 bars and a temperature in the range of about 50-100° C.

According to another aspect of the present invention, the $O_2$ to biomass ratio is between 30:1 and 500:1.

According to another aspect of the present invention, the $CO_2$ flow rate is between 100-700 Kg per hour.

According some embodiments of the present invention, the drying process is optionally performed with addition of powdering agent or anti-caking agent selected from magnesium stearate, lactose, lecithin, talc, hydroxypropyl methylcellulose, micro-crystalline cellulose, sodium alginate, sodium aluminosilicate, silicone hydroxide, chitosan and the like and combination of powdering agents or anti-caking agents thereof.

According to some embodiments of the present invention, the fucoxanthin-rich oleoresin is further refined by additional SCF extraction sequences (e.g., up to 5 extractions) optionally in combination with liquid chromatography.

According to another aspect of the present invention, the remaining pulp after, e.g., the fifth extraction sequence is dissolved in hot water to enable purification of polysaccharides.

According to preferred embodiment of the present invention, the process provided herein affords crude product containing at least about 1.5% fucoxanthin in the dry biomass and at least about 10% fucoxanthin in the extract.

According to some embodiments of the present invention, prior to or after the SCF extraction, the dried biomass is treated enzymatically using enzymes such as proteases and/or extracted with hot water and/or by hot steam and/or treated by washing with buffer solution and/or treated to denature the proteins that are bound to the fucoxanthin.

According to another aspect of the present invention, the remaining pulp (e.g., after the fifth extraction) is dissolved in hot water and/or in acidic aqueous solution.

According to some embodiments of the present invention, fucoxanthin is separated from the polysaccharides and purified by a method selected from filtration, gel-filtration on columns, using for example natural silica beads as medium for filtration, ion-exchange chromatography, liquid chromatography methods including preparative TLC or preparative HPLC and combination of methods thereof to afford highly pure fucoxanthin.

According to some embodiments of the present invention, highly pure fucoxanthin, obtained by, e.g., liquid chromatography, is used alone or in combination with other active ingredients as dietary supplement or as active pharmaceutical ingredient in formulations for preventing, ameliorating or treating a condition or disease selected from cancer, metabolic syndrome including overweight, obesity, high blood cholesterol LDL, high-blood triglycerides, diabetes type II, insulin resistant diabetes, high-blood sucrose, atherosclerosis, dementia, Alzheimer's disease, loss of memory, multiple-sclerosis, depression including environmental-stress, heat stress and general neuroprotection The present invention provides pharmaceutical compositions that contain highly pure fucoxanthin, obtained as described herein, in admixture with pharmaceutically acceptable excipients and, optionally, other therapeutic agents.

According to some embodiments, the pharmaceutical compositions of the present invention that are, e.g., formulated dosage forms, are administered, for example, as tablets, pills, powders, granules, dragees, liquids, suspensions, emulsions, granules, capsules, suppositories, injection preparations (solutions and suspensions), patches and the like.

According to some embodiments of the present invention, the highly pure fucoxanthin is used alone or in combination with other active ingredients in cosmetic preparations such as ointments, gels, creams, solutions, emulsions, lotions and the like for topical or other forms of administration to be used as anti-aging, skin-whitening, skin protection and other cosmetic uses.

In some embodiments, pharmaceutical compositions comprising the fucoxanthin of the present invention are prepared by mixing said fucoxanthin with at least one additional active ingredient selected from absorption accelerators, binders, bulking agents, carriers, coating agents, diluents, disintegrants, extenders, fillers, flavoring agents, lubricants, surface-active agents, wetting agents and the like.

According to some embodiments of the present invention, nutraceuticals, dietary supplements or food preparations comprising the fucoxanthin and/or the polysaccharides of the present invention are prepared by mixing said fucoxanthin and/or polysaccharides with food ingredients such as sugars and starches, dietary fibers, lipids, amino acids, proteins such as protein isolates or protein hydtrolyzates, lactic acid, vitamins, minerals and other ingredients that are commonly used in such preparations.

According to some embodiments of the present invention, the nutraceuticals, dietary supplements or food preparations of the present invention may include, for example, a beverage, a soup, a snack, a dairy product and the like.

Reference is now made to the following examples, which, together with the above description, serve to illustrate the invention without limiting its scope. Additional objects, advantages, and novel features of the present invention will become apparent to one ordinarily skilled in the art.

EXAMPLES

Example 1

This example details the cultivation of the microalgae *Phaeodactylum*, wild type strain 646.

The microalgae *Phaeodactylum*, wild type strain 646, was cultivated under artificial light in agar plates and tubes and transferred into Erlenmeyer flasks and 5 liter round glass flasks. Cultures were then transferred into 3 liter columns and cultivated. The correlation between illumination conditions (shade vs. full sunlight), dry weight accumulation and fucoxanthin accumulation have been studied. Table 3 below details the growth medium compounds that were added to the liquid stock that had initial concentration of 30 g/L and final concentration of 30 mg/L.

A blend of 34 g of salts was added to 980 mL de-ionized water along with potassium nitrate, potassium dihydrogen phosphate and a blend of microelements. The volume was adjusted to 1 L and the mixture was autoclaved. After cooling, 1 mL each of ferric citrate and 20 mM Tris buffer (pH 7.6) were added. Table 3 below details the initial concentrations of the compounds that were added.

TABLE 3

| Compound | Initial concentration |
|---|---|
| Salts blend | 34 g/L |
| KNO$_3$ | 2 g/L |
| KH$_2$PO$_4$ | 70 mg/L |

TABLE 3-continued

| Compound | Initial concentration |
|---|---|
| Ferric citrate | 1 ml/L |
| Citric acid | 42.8 µM |
| Na$_2$SiO$_3$ 9H$_2$O | 1 ml/L |
| Microelements blend | 1 ml/l |
| Vitamins (soluble) | 0.5 ml/L |

Table 4 below details the quantities and initial concentrations of the microelements that were added to the 1 L solution:

TABLE 4

| Compound | Quantity (g) | Initial concentration, µM |
|---|---|---|
| ZnSO$_4$ 7H$_2$O | 0.22 | 0.77 |
| CuSO$_4$ 5 H$_2$O | 0.08 | 0.31 |
| Na$_2$MoO$_4$ 2 H$_2$O | 0.39 | 1.61 |
| H$_3$BO$_3$ | 2.86 | 46.3 |
| MnCl$_2$ 4 H$_2$O | 1.81 | 9.15 |
| CO(NO$_3$)$_2$ 6 H$_2$O | 0.05 | 0.17 |

Table 5 below details the quantities and initial concentrations of the vitamins that were added:

TABLE 5

| Compound | Quantity | Initial concentration |
|---|---|---|
| Vitamin B12 | 1 ml | 1 g/L |
| Biotin | 1 ml | 1 g/L |
| Thiamine HCl | 200 mg | 0.2 g/L |

Example 2

This example details the production of fucoxanthin in columns.

Four columns were loaded each with initial concentration of 0.4 g/L stock solution. Column No. 1 was 50-60% shaded every day until 17:00 hours. Column No. 2 had the light scattered to the "green" wavelength group by filtering through a green-red filter. Column No. 3 had the light scattered to the "blue" wavelength group by filtering through a blue filter. Column No. 4 was not shaded and instead it was subjected to full sunlight. Cultivation was carried out at temperatures of 24-25° C. with a flux of 1% CO$_2$. The following Table 6 below includes data of results measured after two weeks of cultivation.

TABLE 6

| Column No. | Light scattering | Dry weight (g/L) | Fucoxanthin (mg/L) | Fucoxanthin (%) |
|---|---|---|---|---|
| 1 | Shade | 5.3 | 46.1 | 0.87 |
| 2 | Green | 5.7 | 68.4 | 1.2 |
| 3 | Blue | 7.1 | 99.4 | 1.4 |
| 4 | Full sunlight | 6.5 | 40.9 | 0.63 |

Example 3

This example describes the cultivation of the microalgae *Isochrysis* sp, wild type.

The microalgae *Isochrysis* sp. wild type, was cultivated under artificial light in agar plates and tubes and transferred into Erlenmeyer flasks and 5 L round glass flasks. Then, the cultures were transferred into 7 L plastic sleeves to form solutions with maximal concentration of 6 g/L and cultivated under full sunlight. The cultures were collected and diluted to a concentration of 2 g/L and seeded in plastic bags. The correlation between the illumination conditions (wavelength), dry weight accumulation and fucoxanthin production have been studied.

Table 7 below details the content of the growth medium, wherein the initial stock concentration was 30 g/L and the final stock medium concentration was 30 mg/L.

TABLE 7

| Compound | Initial concentration |
| --- | --- |
| Blend of salts | 34 g/L |
| $KNO_3$ | 0.1 g/L |
| $KH_2PO_4$ | 35 mg/L |
| Ferric citrate | 1 mL/L |
| $Na_2SiO_3\ 9H_2O$ | 1 mL/L |
| Microelements blend | 1 mL/L |
| Vitamins, soluble | 0.5 mL/L |

34 g of salts blend was added to 980 mL of de-ionized water along with potassium nitrate ($KNO_3$) and potassium dihydrogen phosphate ($KH_2PO_4$) and microelements blend. The volume was adjusted to 1 L and the mixture was autoclaved. After cooling, 1 mL each of ferric citrate and 20 mM Tris buffer (pH 7.6) were added.

Example 4

This example demonstrates the cultivation of *Isochrysis* sp. and of *Amphora* sp.

Colonies of *Isochrysis* sp. and of *Amphora* sp. were grown on agar, in petri dishes. The material was transferred into tubes containing artificial sea water medium. Cultures were diluted from the test tubes into the flasks and further to polyethylene sleeves and grown under artificial light and injection of filtered air enriched with 1% $CO_2$.

Cultures grown in sleeves were transferred into outdoor 100 liter flat panels, or sleeves containing 10-15 liters. The day of transferring the cultures into 100 liter flat panels was designated as culture age day 0.

The cultures were sampled daily and their dry weight and fucoxanthin concentration were determined. The growth was generally divided into two stages. First the growth conditions were set to support optimal and fast growth and acquisition of biomass. After 5-7 days of fast growth, the algae were transferred into the second production stage, which was the fucoxanthin induction stage.

Example 5

This example details the production of fucoxanthin in sleeves.

Four sleeves were seeded at initial concentration of 2 g/L. The first sleeve was 50-70% shaded every day until 17:00 hours. The second sleeve had light scattered to the "green" wavelength group by filtering through a green-red filter. The third sleeve had light scattered to the "blue" wavelength group by filtering through a blue filter. The fourth was not shaded and instead it was subjected to full sunlight. Table 8 below details the cultivation data after 10 days of growth:

TABLE 8

| Sleeve No. | Light scattering | Dry Weight (g/L) | Fucoxanthin (mg/L) | Fucoxanthin (%) |
| --- | --- | --- | --- | --- |
| 1 | Shade | 4.4 | 57.2 | 1.3 |
| 2 | Green | 5.5 | 121 | 2.2 |
| 3 | Blue | 5.9 | 141.6 | 2.4 |
| 4 | Full sunlight | 4.8 | 52.8 | 1.1 |

Example 6

This example details the harvest, post processing and extraction.

The algae cultures were collected and spin down using a centrifuge. The pelleted algae paste, containing about 30% solids, was washed with fresh water and re-suspended in water while mixing, frozen and freeze-dried. After freeze drying, 1% of silicon dioxide was added to the biomass powder which was further refined and homogenized by air pressure milling. The dry biomass powder (4.2 Kg), containing 2% fucoxanthin (84 g), was extracted by super-critical-fluid $CO_2$ extraction.

Table 9 below summarizes the SCF-$CO_2$ extraction results:

TABLE 9

| Initial quantities | | Separator 1 | | | Separator 2 | | | Total | |
| --- | --- | --- | --- | --- | --- | --- | --- | --- | --- |
| Weight | Fuco | Weight | g | % | Weight | g | % | g | Recovery % |
| 4.2 Kg | 84 g | 606 g | 74.8 | 12.3 | 95.7 | 4.0 | 4.2 | 78.8 | 93.8 |

Fuco = Fucoxanthin

The SCF extraction of 4.2 Kg of biomass powder containing 84 g (2%) fucoxanthin resulted in 606 g fucoxanthin oleoresin (separator 1)+95.7 g fucoxanthin oleoresin (separator 2)=701.7 grams of fucoxanthin oleoresin containing 11.2% fucoxanthin. Thus, the recovery of fucoxanthin was: 74.8 g (separator 1)+4.0 g (separator 2)=78.8 g fucoxanthin (93.8%).

Example 7

This example details the extraction of fucoxanthin using an organic solvent.

The biomass powder was incubated twice in absolute ethanol for 4 hours at ambient temperature and extracted. The extract was partitioned by liquid/liquid extraction with hexane. The solvents were removed by vacuum distillation.

Example 8

This example details the HPLC method for the analysis of fucoxanthin.

Samples were dissolved in a 1:1:1 solvent mixture of acetone/methanol/hexane or in acetonitrile and diluted in same solvent mixture or solvent respectively. Measurements of O.D values were carried out at peak absorbance level of fucoxanthin (450 nm).

Data Relating to Fucoxanthin Separation by HPLC:
Column: C18 250×4.6
Wave lengths: 450 nm
Flow rate: 0.8 mL/min.
Sampler temperature: 15° C.; Column temperature: 28° C.
Mobile phase: (A)—methanol 85%+0.5M ammonium acetate; (B)—acetonitrile: water (90:10); (C)—ethyl acetate.
Run time: 35 min.
Table 10 below details the HPLC gradient used:

TABLE 10

| Time (min.) | A (%) | B (%) | C (%) |
|---|---|---|---|
| 0 | 60 | 40 | 0 |
| 2 | 0 | 100 | 0 |
| 7 | 0 | 80 | 20 |
| 17 | 0 | 50 | 50 |
| 21 | 0 | 30 | 70 |
| 29.5 | 0 | 100 | 0 |
| 30 | 60 | 40 | 0 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An improved process for producing fucoxanthin or fucoxanthin and polysaccharides from microalgae comprising the steps of: (a) cultivating the microalgae medium using inducers to enable rapid cell growth for enhanced production of fucoxanthin or fucoxanthin and polysaccharides, wherein the inducers comprise adding to the growth medium at least one brassinosteroidal hormone selected from the group consisting of auxins and cytokinins and inducing a stress condition of applying specific light wavelength of blue-green; (b) harvesting and drying the algal culture to produce a dry culture; (c) carrying out air pressure milling to crack the cell walls of the algae; (d) extracting the dry culture to produce extracts rich in fucoxanthin or fucoxanthin and polysaccharides; and (e) separating the extraction mixture into a biomass fraction and a fucoxanthin-rich oleoresin or fucoxanthin-rich oleoresin and polysaccharide-rich extract and optionally further purifying said fucoxanthin-rich oleoresin or fucoxanthin-rich oleoresin and polysaccharide-rich extract.

2. The process of claim 1, wherein the algal culture is selected from *Phaeodactylum* sp., *Isochrysis* sp., *Amphora* sp., *Naviculla lensi*, *Naviculla incerta* and *Chaeotocerous* sp.

3. The process of claim 1, wherein cultivating the microalgae is carried out using at least one additional stress condition selected from nitrogen or nitrate starvation, phosphorous starvation, adding $H_2O_2$, applying heat, using higher pH, adding chlorine ions, exposing the medium to ozone and combination of stress conditions thereof.

4. The process of claim 1, wherein harvesting the microalgae is carried out by separating the microalgae from the aqueous mixture by centrifugation and optionally re-centrifugation followed by drying.

5. The process of claim 4, wherein the algal culture is dried by at least one method selected from lyophilization, spray drying, evaporation, air or vacuum drying, exposure to hot air, refractory window belt drying, drying in an oven and combination of methods thereof.

6. The process of claim 4, wherein, the drying process is performed with addition of powdering agent or anti-caking agent selected from magnesium stearate, lactose, lecithin, talc, hydroxypropyl methylcellulose, microcrystalline cellulose, sodium alginate, sodium aluminosilicate, silicone hydroxide, chitosan and combination of powdering agents or anti-caking agents thereof.

7. The process of claim 4, wherein the harvested biomass is concentrated into a solid, washed with water in order to reduce salinity and optionally re-centrifuged to afford a product containing 10-45% weight/volume solids.

8. The process of claim 4, wherein the supernatant obtained by centrifugation and optionally re-centrifugation of the harvested biomass is used for purification of secreted polysaccharides.

9. The process of claim 1, wherein fucoxanthin is separated from the proteins by extraction using at least one organic solvent and/or supercritical fluid (SCF) liquid CO2.

10. The process of claim 9, wherein the at least one organic solvent used for extraction is selected from ethanol, isopropyl alcohol, n-butanol, diethyl ether, diisopropyl ether, n-pentane, n-hexanes, n-heptane, cyclohexane, petroleum ether, tetrahydrofuran, methyltetrahydrofuran, acetonitrile, acetone, methylethyl ketone, methylisobutyl ketone, ethyl acetate, n-propyl acetate, isopropyl acetate and mixtures of solvents thereof.

11. The process of claim 1, which affords a product containing at least 1.5% weight/weight fucoxanthin in the dry biomass and at least 10% weight/weight fucoxanthin in the extract.

12. The process of claim 9, wherein the remaining pulp after the extraction is dissolved in hot water to enable purification of polysaccharides.

13. The process of claim 9, wherein prior to or after the SCF extraction, the dried biomass is treated enzymatically using enzymes and/or extracted with hot water and/or by hot steam and/or treated by washing with buffer solution and/or treated to denature the proteins that are bound to the fucoxanthin.

14. The process of claim 1, wherein the polysaccharides are separated and purified by a method selected from filtration, gel-filtration on columns using natural silica beads as medium for filtration, ion-exchange chromatography, a liquid chromatography method and combination of methods thereof.

15. The process of claim 1, wherein the fucoxanthin-rich oleoresin is further refined and separated from the fatty acids by additional SCF sequences, optionally in combination with liquid chromatography to afford purified fucoxanthin.

16. The process of claim 1, wherein the at least one brassinosteroidal hormone is auxin.

17. The process of claim 4, wherein the liquid chromatography method is selected from preparative TLC and preparative HPLC.

* * * * *